United States Patent [19]

Schlaf

[11] 4,057,638
[45] Nov. 8, 1977

[54] BENZOTHIAZOLE ALLOPHANATE FUNGICIDES

[75] Inventor: Thomas Fulton Schlaf, Wilmington, Del.

[73] Assignee: E. I. Du Pont de Nemours and Company, Wilmington, Del.

[21] Appl. No.: 732,746

[22] Filed: Oct. 15, 1976

Related U.S. Application Data

[63] Continuation-in-part of Ser. No. 593,107, July 3, 1975, abandoned.

[51] Int. Cl.² ................ A01N 9/12; A01N 9/22; C07D 277/82
[52] U.S. Cl. .................... 424/270; 260/305; 424/DIG. 8
[58] Field of Search ............ 424/270, DIG. 8; 260/305

[56] References Cited

U.S. PATENT DOCUMENTS

| | | | |
|---|---|---|---|
| 2,833,689 | 5/1958 | Gerjovich | 424/270 |
| 3,551,441 | 12/1970 | Zakaria | 424/270 X |
| 3,725,428 | 4/1973 | Janiak | 424/270 X |

FOREIGN PATENT DOCUMENTS

| | | |
|---|---|---|
| 47-44,622 | 11/1972 | Japan. |
| 46-39,858 | 11/1971 | Japan. |

OTHER PUBLICATIONS

Chem. Pharm. Bull. 20, 2626-2633, (1972) Nagano et al.

*Primary Examiner*—Allen J. Robinson

[57] ABSTRACT

Compounds of the formula

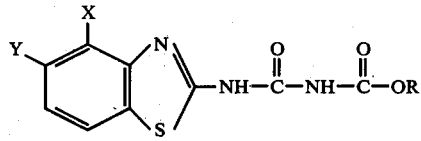

where
either X or Y may independently be hydrogen, methyl, ethyl, fluorine, chlorine, or bromine; and
R is alkyl of 1 to 4 carbon atoms, are useful as fungicides. A representative compound is methy 4-(4-chlorobenzothiazol-2-yl)allophanate.

28 Claims, No Drawings

BENZOTHIAZOLE ALLOPHANATE FUNGICIDES

RELATED APPLICATIONS

This application is a continuation-in-part of my co-pending application U.S. Ser. No. 593,107, filed July 3, 1975 now abandoned.

BACKGROUND OF THE INVENTION

This invention relates to the use of novel benzothiazole allophanates as fungicides. In particular, such fungicides are useful for the control of such plant diseases as powdery mildew and especially cucumber powdery mildew.

The prior art in an article in Chem. Pharm. Bull. 20, 2626 (1972) (Sankyo Chem. Co.) discloses the reaction of 2-aminobenzothiazole and ethoxycarbonyl isothiocyanate; no use is reported for the product.

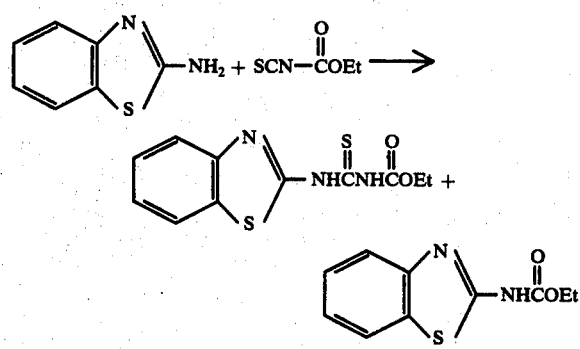

The preparation of the benzimidazole allophanate I from ethoxycarbonylisocyanate has been reported [Chem. Ber., 107, 62 (1974)], although again no use has been disclosed.

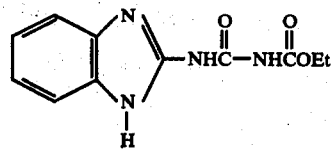

These references do not suggest the compounds of the instant invention nor do they disclose activity in controlling powdery mildew such as cucumber powdery mildew.

SUMMARY OF THE INVENTION

Injury due to fungi is prevented by application to the locus to be protected, a fungicidally effective amount of the compound described below; it should be emphasized that the compounds are novel. These compounds have systemic fungicidal activity and consequently can be applied directly to the plant parts to be protected, other parts of the plant or to the media in which the plants are growing. It is preferred to apply the compound directly to the plant. However, all such applications are to be included in the term "applying to plants" as used herein.

The compounds of the instant invention have the following formula:

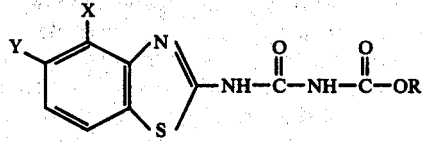

where
X and Y may independently be hydrogen, methyl ethyl, fluorine, chlorine, or bromine; and
R is alkyl of 1 to 4 carbon atoms.

Preferred for their higher fungicidal activity are the compounds of Formula II where X or Y may independently by hydrogen, methyl or chlorine.

Similarly preferred for their higher fungicidal activity are the compounds of Formula II where R is methyl or ethyl.

Most highly preferred for their ease of synthesis or superior fungicidal activity are the compounds of Formula II where X or Y may independently be hydrogen, methyl, or chlorine, and R is methyl or ethyl.

Specifically preferred for their outstanding fungicidal activity are:
1. Methyl 4-(4-chlorobenzothiazol-2-yl)allophanate, m.p. 319°–320° C;
2. Methyl 4-(4-methylbenzothiazol-2-yl)allophanate, m.p. 272°–280° C;
3. Methyl 4-(benzothiazol-2-yl)allophanate, m.p. 338°–340° C;
4. Methyl 4-(5-chlorobenzothiazol-2-yl)allophanate, m.p. 395° C;
5. Methyl 4-(5-chloro-4-methylbenzothiazol-2-yl)allophanate, m.p. >275° C (dec).

DETAILED DESCRIPTION OF THE INVENTION

Synthesis

The fungicidally active compounds of Formula II can be prepared by conventional means. For example, they can be prepared by the reaction of an alkoxycarbonyl isocyanate made according to the method of A. J. Speziale, L. R. Smith and J. E. Fedder J. Org. Chem., 30, 4307(1965) with a 2-aminobenzothiazole prepared by the method of C. F. H. Allen, Org. Syn. III, 76 (1955).

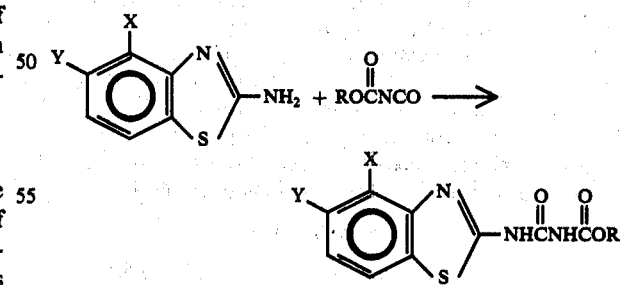

wherein
X and Y may independently be hydrogen, methyl, ethyl, fluorine, chlorine or bromine; and
R is alkyl of 1 to 4 carbon atoms either straight chain or branched.

The above reaction is carried out by bringing the reactants together in approximately stoichiometric proportions in a suitable organic solvent such as acetonitrile, acetone, benzene, butyl chloride, chlorobenzene, chloroform, o-dichlorobenzene, dichloroethylene, dimethylformamide, dioxane, ethyl acetate, ethyl ether, ethyl formate, methylene chloride, tetrahydrofuran, toluene, trichloroethane, trichloroethylene or xylene. No catalyst is needed but in many cases it is desirable to use a slight excess of the isocyanate reactant, for example 5–10% molar excess. Ordinarily temperatures in the range of 20°–35° C are employed for this reaction; pressure is ambient. The product resulting directly from this reaction is generally obtained by filtration or evaporation of the solvent and is usually of purity satisfactory for direct usage.

The following examples further illustrate the methods for synthesis of these novel, fungicidal compounds. All parts are by weight and all temperatures are in degrees centigrade unless otherwise indicated.

EXAMPLE 1

Five and one half parts by weight of methoxycarbonyl isocyanate was added gradually with stirring to a solution at room temperature of nine parts by weight of 2-amino-4-chlorobenzothiazole dissolved in 200 parts by weight of dioxane. After stirring the reaction mixture at room temperature overnight, a product was isolated by filtration giving a 45% yield of methyl 4-[4-chlorobenzothiazol-2-yl]allophanate having a melting point of 319°–20° C.

Analysis: Calc'd for $C_{10}H_8N_3Cl_1O_3S_1$: C 42.04, H 2.82, N 14.71. Found: C 41.62, H 3.19, N 14.03.

EXAMPLE 2

Three and one half parts by weight of methoxycarbonyl isocyanate was added gradually with stirring to a solution at room temperature of 4½ parts by weight of 2-aminobenzothiazole dissolved in 150 parts by weight of methylene chloride. After stirring the reaction mixture at room temperature for 12 hours, the product was isolated by filtration giving a 40% yield of essentially pure methyl 4-(benzothiazol-2-yl)allophanate having a melting point of 338°–340° C with decomposition.

Analysis: Calc'd for $C_{10}H_9N_3O_3S$: H 3.61, N 16.72, S 12.76. Found: H 3.59, N 16.20, S 13.41.

EXAMPLE 3

Two and one half parts by weight of methoxycarbonyl isocyanate was added gradually with stirring to a solution of 4 parts by weight of 2-amino-4-methylbenzothiazole dissolved in 250 parts by weight of methylene chloride. The reaction mixture was stirred at room temperature for 12 hours. The solution was concentrated to one fifth the original volume and the solid isolated by filtration to give a 37% yield of methyl 4-(4-methylbenzothiazol-2-yl)allophanate having a melting point of 272°–280° with decomposition.

EXAMPLE 4

A solution of 2 parts by weight of methoxycarbonylisocyanate in 15 parts by weight of methylene chloride was added gradually with stirring to a solution, at room temperature, of 4 parts by weight of 2-amino-5-chloro-4-methylbenzothiazole in 75 parts by weight of methylene chloride and 50 parts by weight of tetrahydrofuran. After stirring the reaction mixture at room temprature overnight, a product was isolated by filtration giving a 40% yield of methyl 4-(5-chloro-4-methylbenzothiazol-2-yl)allophanate having a melting point greater than 275°.

EXAMPLE 5

One part by weight of methoxycarbonyl isocyanate was added gradually with stirring to a solution of 2 parts by weight of 2-amino-5-chlorobenzothiazole in 100 parts by weight of methylene chloride and 50 parts by weight of ethyl ether. After stirring the reaction mixture at room temperature overnight, a product was isolated by filtration giving an 85% yield of methyl 4-(5-chlorobenzothiazol-2-yl)allophanate having a melting point of 395°.

According to the method of Example 1 using the appropriately substituted 2-aminobenzothiazole and the appropriate alkoxycarbonyl isocyanate the compounds in Table I can be prepared.

Table 1 structure: benzothiazole with X, Y substituents and —NHCNHC(=O)(=O)—OR group

| X | Y | R | M.P. |
|---|---|---|---|
| Cl | H | —$C_2H_5$ | 308–10° |
| Cl | H | —$CH(CH_3)_2$ | 310–12° |
| Cl | H | —CH—$C_2H_5$ / $CH_3$ | 315–7° |
| Cl | H | —$C_3H_7$ | 187–8° |
| Cl | H | —$C_4H_9$ | 323–5° |
| H | H | —$C_2H_5$ | 185–6° |
| H | H | —$CH(CH_3)_2$ | 152–3° dec |
| H | H | —CH—$C_2H_5$ / $CH_3$ | 146–7° |
| H | H | —$C_3H_7$ | 162–3° |
| H | H | —$C_4H_9$ | 131–2° |
| $CH_3$ | H | —$C_2H_5$ | 276–8° |
| $CH_3$ | H | —$CH(CH_3)_2$ | 277–9° dec |
| $CH_3$ | H | $CH_3$ | 272–8° dec |
| $CH_3$ | H | —CH—$C_2H_5$ / $CH_3$ | 277–81° dec |
| $CH_3$ | H | —$C_4H_9$ | 270–1° |
| Br | H | $CH_3$ | 302–5° dec |
| F | H | $CH_3$ | 320–9° dec |
| $C_2H_5$ | H | —CH—$CH_2CH_3$ / $CH_3$ | 253–62° |
| $C_2H_5$ | H | $CH(CH_3)_2$ | 264–70° |
| $C_2H_5$ | H | $CH_3$ | 280–2° dec |
| H | F | $CH_3$ | >270° |
| F | Cl | $CH_3$ | >270° |
| H | Br | $CH_3$ | — |
| H | $CH_3$ | $CH_3$ | — |
| H | $C_2H_5$ | $CH_3$ | — |

Utility

In practicing the fungicidal methods of this invention, one or more of the active ingredients is applied to plants for the control of fungi at a dosage sufficient to control plant disease. Accordingly, these compositions and methods are applicable for the protection of living plants such as vegetables, field crops, ornamental plants and fruit-bearing trees. Some of these compositions are also effective when applied directly to the soil for controlling plant pathogenic fungi. The compounds of this invention are especially effective in controlling Erysiphaceae, powdery mildew fungi.

In application to plants, disease control is obtained in most instances by applying the active compound at a dosage or rate from about 0.1 to 10.0 kilograms per hectare. In application directly to the soil for use as a systemic fungicide, in most instances, the dosage or rate is from about 1 to 75 kilograms per hectare. The optimum dosage can be determined in each instance by one of the means conventional in the art. The optimum amount is, of course, determined by and dependent upon the particular fungicidal compound selected, the method of application, the climatic conditions, and, in the case of application to vegetation, the state and condition of growth of the vegetation to be treated.

EXAMPLE 6

Two-week old Straight Eight variety cucumber plants were sprayed uniformly to the point of run-off with a dispersion consisting of acetone, water, a surfactant and the compound of this invention (see below) at 80, 16, and 3.2 ppm. The following day all plants were inoculated with a distilled water suspension of cucumber powdery mildew (*Erysiphe cichoracearum*) conidia. After 9 days of incubation in the greenhouse, disease ratings were made by a visual estimate of the percentage of the inoculated leaf area that was diseased. This is a preventive test because chemicals were applied prior to inoculation. A summary of readings, based on three replicate plants for each treatment, is given below.

|  | Percent disease control | | |
| --- | --- | --- | --- |
|  | 80 ppm | 16 ppm | 3.2 ppm |
| methyl 4-(4-chlorobenzothiazol-2-yl)allophanate | 100 | 100 | 96 |

EXAMPLE 7

Methyl 4-(5-chlorobenzothiazol-2-yl)allophanate, when sprayed on cucumber plants in accordance with the procedure in Example 6, prevents cucumber powdery mildew (*Erysiphe cichoracearum*) as shown by the following readings:

| Percent Disease Control | | |
| --- | --- | --- |
| 80 ppm | 16 ppm | 3.2 ppm |
| 100 | 100 | 88 |

EXAMPLE 8

Methyl 4-(5-chloro-4-methylbenzothiazol-2-yl)-allophanate, when sprayed on cucumbers in accordance with the procedure in Example 6, prevents cucumber powder mildew (*Erysiphe cichoracearum*) as shown by the following readings:

| Percent Disease Control | | |
| --- | --- | --- |
| 80 ppm | 16 ppm | 3.2 ppm |
| 100 | 99 | 88 |

EXAMPLE 9

Methyl 4-(4-chlorobenzothiazol-2-yl)allophanate is prepared in accordance with the procedure of Example 1.

The following wettable powder, when dispersed in water and sprayed on apple trees, prevents apple powdery mildew (*Podosphaera leucotricha*).

| Ingredient: | Percent by Weight |
| --- | --- |
| Methyl 4-(4-chlorobenzothiazol-2-yl)-allophanate | 20 |

-continued

| Ingredient: | Percent by Weight |
| --- | --- |
| Sodium lauryl sulfate | 0.25 |
| Sodium lignin sulfonate | .5 |
| Kaolin clay | 79.25 |

EXAMPLE 10

Methyl 4-(benzothiazol-2-yl)allophanate is prepared in accordance with the procedure of Example 1.

The following dust composition, when dusted on the ground where cucumbers are planted, controls cucumber powdery mildew (*Erysiphe cichoracearum*).

| Ingredient: | Percent by Weight |
| --- | --- |
| Methyl 4-(benzothiazol-2-yl)allophanate | 30 |
| Talc | 70 |

EXAMPLE 11

Methyl 4-(4-methylbenzothiazol-2-yl)allophanate is prepared in accordance with the procedure of Example 1.

The following dust composition, when dusted on the surface of the soil in which cucumbers are planted, controls cucumber powdery mildew (*Erysiphe cichoracearum*).

| Ingredient: | Percent by Weight |
| --- | --- |
| Methyl 4-(4-methylbenzothiazol-2-yl)-allophanate | 30 |
| Ground phosphate rock | 70 |

EXAMPLE 12

Methyl 4-(4-chlorobenzothiazol-2-yl)allophanate is prepared in accordance with the procedure of Example 1.

The following dust composition when dusted on the surface of the soil in which melons are grown prevents watermelon powdery mildew (*Erysiphe cichoracearum*).

| Ingredient: | Percent by Weight |
| --- | --- |
| Methyl 4-(4-chlorobenzothiazole-2-yl)-allophanate | 30 |
| Stearated calcium carbonate | 70 |

Useful formulations of the compounds of Formula I can be prepared in conventional ways. They include dusts, solutions, suspensions, wettable powders, and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1 to 99% by weight of active ingredient(s) and at least one of (a) about 0.1 to 20% surfactant(s) and (b) about 5 to 99% solid or liquid diluent(s). More specifically, they will contain these ingredients in the following approximate proportions:

|  | Percent by Weight | | |
| --- | --- | --- | --- |
|  | Active Ingredient | Diluent(s) | Suffactant(s) |
| Wettable Powders | 20-90 | 0-74 | 1-10 |
| Oil Suspensions, Solutions | 5-50 | 40-95 | 0-15 |
| Aqueous Suspensions | 10-50 | 40-84 | 1-20 |
| Dusts | 1-25 | 70-99 | 0-5 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc. New York, 1964, list surfactants and recommended uses. All formulations can contain minor amounts of additives to reduce foam, caking, corrosion, microbiological growth, control pH, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:
- J. B. Buchanan, U.S. Pat. No. 3,576,834, Apr. 27, 1971, Col. 5 Line 36 through Col. 7 Line 70 and Ex. 1-4, 17, 106, 123-140.
- R. R. Shaffer, U.S. Pat. No. 3,560,616, Feb. 2, 1971, Col. 3 Line 48 through Col. 7 Line 26 and Examples 3-9, 11-18.
- E. Somers, "Formulation", Chapter 6 in Torgeson, "Fungicides", Vol. I, Academic Press, New York, 1967.

EXAMPLE 13

| Wettable Powder | |
| --- | --- |
| methyl 4-(4-chlorobenzothiazol-2-yl)allophanate | 50% |
| dioctyl sodium sulfosuccinate | 1.5% |
| sodium ligninsulfonate | 3% |
| low viscosity methyl cellulose | 1.5% |
| attapulgite | 44% |

The ingredients are thoroughly blended, passed through an air mill to produce an average particle size well under 15 microns, reblended, and sifted through a U.S.S. No. 50 sieve (0.3 mm opening) before packaging.

All compounds of the invention may be formulated in the same manner.

EXAMPLE 14

| Aqueous Suspension | |
| --- | --- |
| methyl 4-(4-methylbenzothiazol-2-yl)allophanate | 25% |
| hydrated attapulgite | 3% |
| crude calcium ligninsulfonate | 10% |
| disodium hydrogen phosphate | 0.5% |
| sodium dihydrogen phosphate | 0.5 |
| water | 61% |

The ingredients are ground together in a ball or roller mill until the solid particles have been reduced to diameters under 10 microns.

EXAMPLE 15

| Oil Suspension | |
| --- | --- |
| methyl 4-(benzothiazol-2-yl)allophanate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

| High Strength Concentrate | |
| --- | --- |
| methyl 4-(benzothiazol-2-yl)allophanate | 98.5% |
| silica aerogel | 0.5% |
| synthetic amorphous fine silica | 1.0% |

The ingredients are blended and air milled to produce a high strength concentrate. This material may then be formulated in a variety of ways.

EXAMPLE 17

| Dust | |
| --- | --- |
| high strength concentrate, Example 16 | 10.2% |
| pyrophyllite, powdered | 89.8% |

The ingredients are thoroughly blended and packaged for use.

EXAMPLE 18

| Wettable Powder | |
| --- | --- |
| methyl 4-(4-chlorobenzothiazol-2-yl)allophanate | 80% |
| sodium alkylnaphthalenesulfonate | 2% |
| sodium ligninsulfonate | 2% |
| synthetic amorphous silica | 3% |
| kaolinite | 13% |

The ingredients are combined and passed through a hammer mill to produce a wettable powder with average particle size below 20 microns. After a final blending, the product is sifted through a USS No. 50 screen (0.3 mm opening) and packaged.

What is claimed is:
1. A compound of the formula:

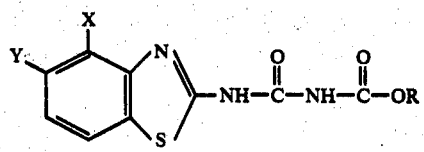

where
- X or Y may independently be hydrogen, methyl, ethyl, fluorine, chlorine or bromine; and
- R is alkyl of 1 to 4 carbon atoms.

2. The compound of claim 1 wherein X or Y is independently selected from the group consisting of hydrogen, methyl and chlorine.

3. The compound of claim 1 wherein R is methyl or ethyl.

4. The compound of claim 1 wherein X or Y is independently selected from the group consisting of hydrogen, methyl and chlorine and R is selected from the group consisting of methyl and ethyl.

5. The compound of claim 1 which is methyl 4-(4-chlorobenzothiazol-2-yl)allophanate.

6. The compound of claim 1 which is methyl 4-(benzothiazol-2-yl)allophanate.

7. The compound of claim 1 which is methyl 4-(4-methylbenzothiazol-2-yl)allophanate.

8. The compound of claim 1 which is methyl 4-(5-chlorobenzothiazol-2-yl)allophanate.

9. The compound of claim 1 which is methyl 4-(5-chloro-4-methylbenzothiazol-2-yl)allophanate.

10. A composition for the control of fungi consisting essentially of a fungicidally effective amount of a compound of claim 1 and at least one of (a) a surface-active agent and (b) a solid or liquid diluent.

11. A composition for the control of fungi consisting essentially of a fungicidally effective amount of a compound of claim 2 and at least one of (a) a surface-active agent and (b) a solid or liquid diluent.

12. A composition for the control of fungi consisting essentially of a fungicidally effective amount of a compound of claim 3 and at least one of (a) a surface-active agent and (b) a solid or liquid diluent.

13. A composition for the control of fungi consisting essentially of a fungicidally effective amount of a compound of claim 4 and at least one of (a) a surface-active agent and (b) a solid or liquid diluent.

14. A composition for the control of fungi consisting essentially of a fungicidally effective amount of the compound of claim 5 and at least one of (a) a surface-active agent and (b) a solid or liquid diluent.

15. A composition for the control of fungi consisting essentially of a fungicidally effective amount of the compound of claim 6 and at least one of (a) a surface-active agent and (b) a solid or liquid diluent.

16. A composition for the control of fungi consisting essentially of a fungicidally effective amount of the compound of claim 7 and at least one of (a) a surface-active agent and (b) a solid or liquid diluent.

17. A composition for the control of fungi consisting essentially of a fungicidally effective amount of the compound of claim 8 and at least one of (a) a surface-active agent and (b) a solid or liquid diluent.

18. A composition for the control of fungi consisting essentially of a fungicidally effective amount of the compound of claim 9 and at least one of (a) a surface-active agent and (b) a solid or liquid diluent.

19. A method of preventing injury to plants due to fungi consisting essentially of applying to the plants a fungicidally effective amount of a compound of claim 1.

20. A method of preventing injury to plants due to fungi consisting essentially of applying to the plants a fungicidally effective amount of a compound of claim 2.

21. A method of preventing injury to plants due to fungi consisting essentially of applying to the plants a fungicidally effective amount of a compound of claim 3.

22. A method of preventing injury to plants due to fungi consisting essentially of applying to the plants a fungicidally effective amount of a compound of claim 4.

23. A method of preventing injury to plants due to fungi consisting essentially of applying to the plants a fungicidally effective amount of the compound of claim 5.

24. A method of preventing injury to plants due to fungi consisting essentially of applying to the plants a fungicidally effective amount of the compound of claim 6.

25. A method of preventing injury to plants due to fungi consisting essentially of applying to the plants a fungicidally effective amount of the compound of claim 7.

26. A method of preventing injury to plants due to fungi consisting essentially of applying to the plants a fungicidally effective amount of the compound of claim 8.

27. A method of preventing injury to plants due to cucumber powdery mildew consisting essentially of applying to the plants a fungicidally effective amount of the compound of claim 9.

28. A method of preventing injury to plants due to cucumber powdery mildew consisting essentially of applying to the plants a fungicidally effective amount of a compound of claim 1.

* * * * *